United States Patent
Lee et al.

(10) Patent No.: US 7,872,122 B2
(45) Date of Patent: Jan. 18, 2011

(54) PROCESS FOR MAKING BIOLIMUS A9

(75) Inventors: Kwang-Chung Lee, Taoyuan (TW); Ping-Shu Chen, Taipei (TW); Shu-Chuan Lin, Su-Lin (TW); Tzu-Ai Lee, Taoyuan (TW)

(73) Assignee: Chunghwa Chemical Synthesis & Biotech Co., Ltd., Su-Lin, Taipei County (TW)

( * ) Notice: Subject to any disclaimer, the term of this patent is extended or adjusted under 35 U.S.C. 154(b) by 68 days.

(21) Appl. No.: 12/387,754

(22) Filed: May 8, 2009

(65) Prior Publication Data

US 2009/0292118 A1 Nov. 26, 2009

(51) Int. Cl.
*C07D 498/18* (2006.01)

(52) U.S. Cl. ...................................................... 540/456
(58) Field of Classification Search ................... 540/456
See application file for complete search history.

(56) References Cited

U.S. PATENT DOCUMENTS 7,193,078 B2 * 3/2007 Isozaki et al. ............... 540/456

* cited by examiner

*Primary Examiner*—Bruck Kifle

(57) ABSTRACT

A process for making Biolimus A9 comprises reacting sirolimus (or rapamycin) with alkyl benzene sulfonate under the catalyzing of organic base and in the presence of organic solvent to undergo a nucleophilic substitution reaction to obtain the Biolimus A9 with high yield, not only for small-scale laboratory experiment, but also for rendering reproducibility of high yield even after process amplification.

11 Claims, 1 Drawing Sheet

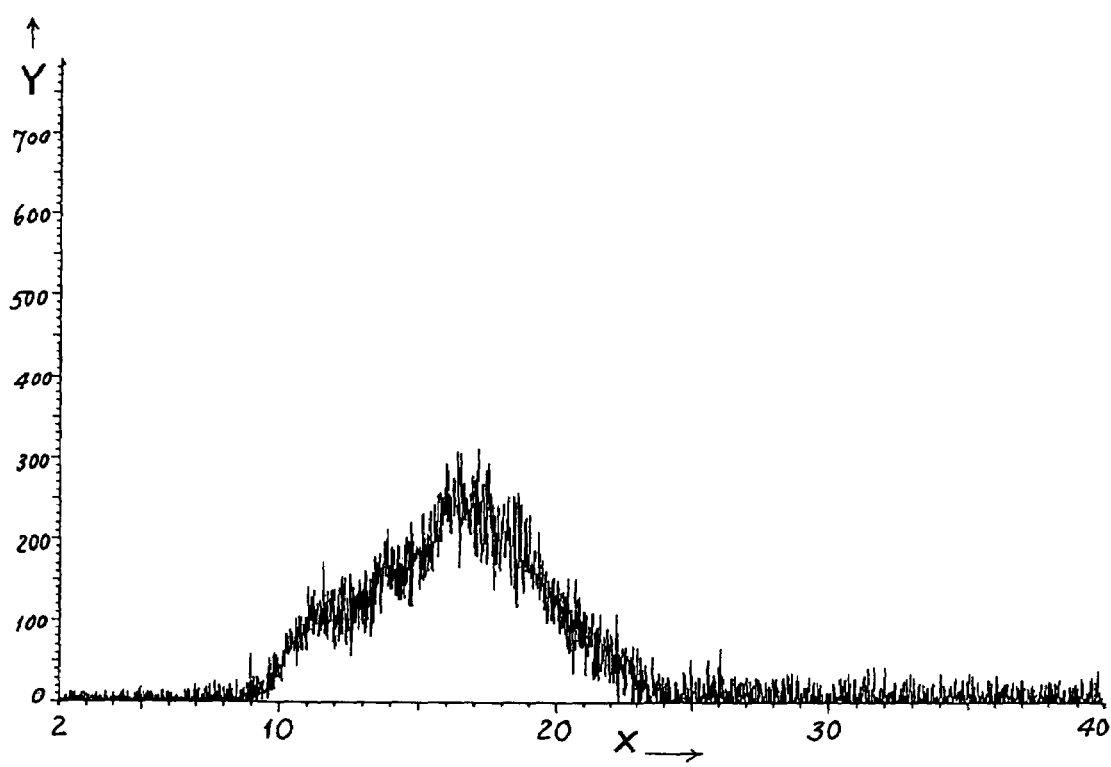

PROCESS FOR MAKING BIOLIMUS A9

BACKGROUND OF THE INVENTION

It is known that Biolimus A9, a rapamycin derivative, is an immunosuppressant, and is also proven to have anti-tumor and anti-fungal effect.

Several prior arts had disclosed the improvements of the product yield of rapamycin derivatives. U.S. Pat. No. 7,193,078 to Isozaki et al. disclosed a process for producing Biolimus A9, giving an example to obtain a yield of 46% by reacting rapamycin with 2-ethoxyethyl trifluoromethane sulfonate (or 2-ethoxyethyl triflate) in an organic solvent.

However, the Isozaki's prior art still has the following drawbacks:

1. Even one example ever showed a 46% yield of Biolimus A9, it however just revealed a small-scale laboratory experiment with only one gram (1.09 mmol) of rapamycin and 1.95g (8.78 mmol) of 2-ethoxyethyl triflate. After amplifying or expanding the process to be larger scale, the yield will be remarkably reduced to thereby decrease the commercial or industrial value of this prior art (Note: The low yield after simulated process amplification will be hereinafter discussed in Examples 3, 4 of this application).
2. Even the reactant of 2-ethoxyethyl triflate is a compound with high activity, it is unstable and will be decomposed such as after being stored for one week at room temperature. Also, the triflate is not UV-absorbable and is therefore unsuitable for process tracking when proceeding the reaction. Such poor properties will affect the material storage, production scheduling and process tracking for commercially making the Biolimus A9.

The present inventor has found the drawbacks of the prior art and invented the present process for making Biolimus A9 efficiently and economically.

SUMMARY OF THE INVENTION

The object of the present invention is to provide a process for making Biolimus A9 by reacting sirolimus (or rapamycin) with alkyl benzene sulfonate under the catalyzing of organic base and in the presence of organic solvent to undergo a nucleophilic substitution reaction to obtain the Biolimus A9 with high yield, not only for small-scale laboratory experiment, but also for rendering reproducibility of high yield even after process amplification.

BRIEF DESCRIPTION OF THE DRAWINGS

The single drawing FIGURE shows a X-ray powder diffractogramm of Biolimus A9 of the present invention, in which the abscissa X indicates 2-Theta-scale, and the ordinate Y describes Lin in Counts.

DETAILED DESCRIPTION

The present invention discloses a process for making Biolimus A9 of structural formula (1) as included in alkyl sirolimus of structural formula (6) (Note: All the structural formulas will be shown in the specification hereinafter presented).

A starting reactant of sirolimus (or rapamycin) of formula (2) is reacted with alkyl benzene sulfonate of formula (3) under the catalyzing of an organic base of trialkyl amine of formula (4) or pyridine of formula (5) and in the presence of an organic solvent to undergo nucleophilic substitution reaction to obtain alkyl sirolimus of formula (6) including Biolimus A9 of formula (1) in accordance with the present invention.

The formulas, definitions and detailed description for the related reactants, radicals, base, solvent and products are further described as follows:

Sirolimus which is represented by the following formula:

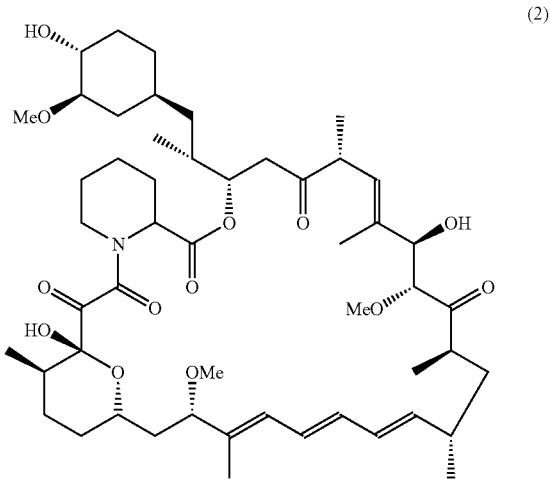

(2)

Alkylbenzene Sulfonate

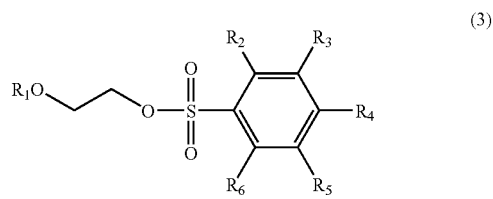

(3)

which renders high stability, high activity and sound tractability to be beneficial for the reaction of the present invention; and wherein: $R_1$ is selected from the group consisting of: alkyl, silyl, alkenyl, alkenylalkyl, alkynyl, alkynylalkyl, aryl, arylalkyl, heteroaryl and heteroarylalkyl; $R_2$, $R_3$, $R_4$, $R_5$ and $R_6$ are each respectively selected from the group consisting of: hydrogen, halogen, nitro group and other substituents.

If such an alkyl benzene sulfonate is typically represented by 2-ethoxyethyl pentafluorobenzene sulfonate, it can be stored, at room temperature, without being decomposed even after one-week storage as checked by NMR spectrographic detection.

Tralkyl Amine

(4)

wherein $R_7$, $R_8$ and $R_9$ are each selected from $C_1$~$C_{10}$ alkyl substituents respectively.

Pyridine

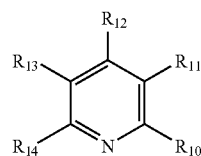
(5)

wherein $R_{10}$, $R_{11}$, $R_{12}$, $R_{13}$ and $R_{14}$ are each respectively selected from: hydrogen and $C_1~C_{10}$ alkyl substituents.

Organic Solvent which may be selected from methylene chloride and other suitable organic solvents.

Alkyl Sirolimus

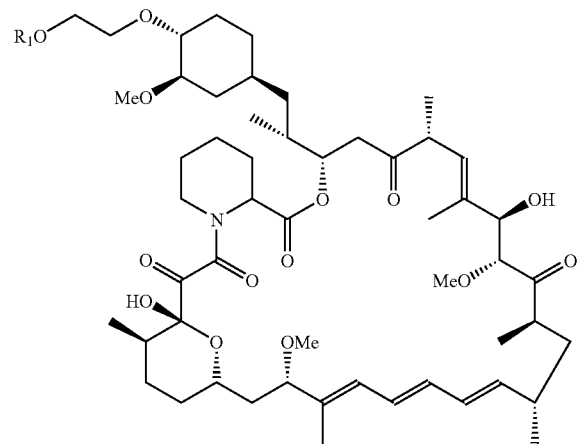
(6)

wherein $R_1$ is selected from the group consisting of: alkyl, silyl, alkenyl, alkenylalkyl, alkynyl, alkynylalkyl, aryl, arylalkyl, heteroaryl and heteroarylalkyl; and when $R_1$ is an ethyl group, the Biolimus A9 of the present invention will be presented as below-mentioned:

Biolimus A9

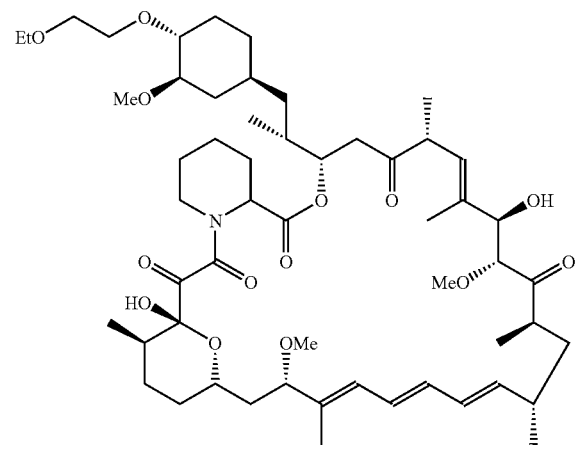
(1)

Reaction Parameters

Quantity of Alkylbenzene Sulfonate: 1~20 equivalents, preferably being 5~10 equivalents, per equivalent of sirolimus.

Reaction Temperature: 40~80° C., preferably being 55~65° C. Reaction Time: 12~72 hours, preferably being 16~30 hours.

After the reaction is completed, the rough product is collected, washed, dried and purified to obtain the Biolimus A9 of the present invention with high yield of 45%.

Since the product Biolimus A9 is a polyene macrolide, which is easily oxidized and decomposed during the storage or material handling.

Accordingly, a proper antioxidant may be homogeneously mixed with the Biolimus A9 to enhance the stability when stored or handled.

The proper antioxidants may be selected from: Butylatd hydroxytoluene (BHT), DL-α-tocopherol, propyl gallate, ascorbyl palmitate, 3-tert-butyl-4-hydroxyanisole, 2-tert-butyl-4-hydroxyanisole, and fumaric acid.

The Butylated hydroxytoluene (BHT) is the most preferable antioxidant adapted for use in the present invention.

The process for making Biolimus A9 in accordance with the present invention will be described in detail in view of the following examples:

EXAMPLE 1

A. Synthesis of 2-ethoxyethyl pentafluorobenzene sulfonate

In a reaction flask, 25 grams (93.8 mmol) of pentafluorobenzene sulfonyl chloride (or pentafluorobenzene sulfochloride) and 86 ml of tetrahydrofuran were added and nitrogen gas was filled into the flask.

The flask is then cooled to 0° C. and is dripped therein with 2-ethoxyethanol (8.5g, 94.5 mmol) and triethyl amine (15 g, 148.5 mmol). After dripping, the reaction solution is stirred for 30 minutes, and then filtered, concentrated and the residue is separated from the solution and further purified by silica gel column chromatography to obtain a colorless oily product of 2-ethoxyethyl pentafluorobenzene sulfonate (26.6 g, 83.1 mmol) having a yield of 88.6%.

B. Synthesis of Biolimus A9

In a reaction flask, 1 g (1.1 mmol) of sirolimus, 7.8 g (60.3 mmol) of ethyl di-isopropyl amine, 3.5 ml of methylene chloride and 2.8 g (8.7 mmol) of 2-ethoxyethyl pentrafluorobenzene sulfonate as previously obtained were added therein.

The reaction mixture in the flask was heated to 60° C. and agitated for 23 hours. It is cooled, and further added therein with ethyl acetate (100 ml) and aqueous solution of hydrochloric acid (1N, 100 ml) under agitation.

Then, it is settled for separating the organic and aqueous layers. The organic layer is collected, and washed with pure water (100 ml) and saturated saline (100 ml). The washed organic liquid is then dried and concentrated. The residue is then separated from the liquid and further purified by silica gel column chromatography to obtain white solid product of Biolimus A9 (0.49 g, 0.5 mmol) with a yield of 45.4%.

EXAMPLE 2

Process Amplification of Example 1B

In a reaction flask, 10 g (10.9 mmol) of sirolimus, 78 g (603.5 mmol) of ethyl di-isopropyl amine, 35 ml of methylene chloride and 28 g (87.4 mmol) of 2-ethoxyethyl pentrafluorobenzene sulfonate were added therein.

The reaction mixture in the flask was heated to 60° C. and agitated for 24 fours. It is cooled, and further added therein with ethyl acetate (500 ml) and aqueous solution of hydrochloric acid (1N, 500 ml) under agitation.

Then, it is settled for separating the organic and aqueous layers. The organic layer is collected, and washed with pure water (500 ml) and saturated saline (400 ml). The washed organic liquid is then dried and concentrated. The residue is then separated from the liquid and further purified by silica gel column chromatography to obtain white solid product of Biolimus A9 (4.8 g, 4.9 mmol) with a yield of 44.5%.

This example is a process amplification of the previous Example 1, Step B, by amplifying or expanding the quantity of each reactant for about 10 times of that of the Example 1 (of small scale).

By the way, the production yield (44.5%) of this Example is still as high as that of the previous Example 1 of small scale. It indicates that the reproducibility of high yield can still be obtained in accordance with the present invention even after process amplification, proving that the present invention is suitable for commercialization or mass production. The product may be further purified to obtain a high-purity final product of Biolimus A9 such as by middle-performance liquid chromatography or the like. The Biolimus A9 thus obtained is identified by the X-ray powder diffractogramm as shown in the single drawing FIGURE as attached herewith.

EXAMPLE 3

Comparative Example for Simulating the Process of the Prior Art of U.S. Pat. No. 7,193,078

A. Synthesis of 2-ethoxyethyl trifluoromethane sulfonate

In a reaction flask, 2-ethoxyethanol (10 g, 111 mmol), methylene chloride (177 ml) and 2,6-dimethyl pyridine (23.8 g, 222.3 mmol) were added into the flask, which is filled therein with nitrogen gas. It is cooled to 0° C. and added dropwise with trifluoromethane sulfonic acid anhydride (37.6 g, 133.4 mmol). After completing the dripping of said sulfonic acid anhydride, the reaction mixture is agitated for one hour and a saturated aqueous solution of ammonium chloride (20 ml) is added and further agitated for 10 minutes.

It is then settled for separating the layers. The organic layer is collected, and is respectively washed with aqueous solution of hydrochloric acid (1N, 100 ml), pure water (100 ml), saturated aqueous solution of sodium bicarbonate (100 ml) and saturated saline (100 ml). The washed organic layer is dried, concentrated and the residue is then separated and further purified with silica gel column chromatography to obtain the oily product of 22.5 g (101.3 mmol) of 2-ethoxyethyl trifluoromethane sulfonate (or 2-ethoxyethyl triflate), with a yield of 91.3%.

B. Synthesis of Biolimus A9

In a reaction flask, sirolimus (1 g, 1.1 mmol), ethyl di-isopropyl amine (7.8 g, 60.3 mmol), methylene chloride (3.5 ml) and 2-ethoxyethyl triflate (2.0 g, 8.8 mmol) as previously made in Example 3A were added into the flask, which is filled with nitrogen gas. The reaction mixture is heated to 60° C. and is agitated for one hour and twenty minutes. Then, it is cooled, added with ethyl acetate (100 ml) and aqueous solution of hydrochloric acid (1N, 100 ml) and is further agitated. After agitation, it is settled for separating the layers. The organic layer is collected and respectively washed with pure water (100 ml), saturated saline (80 ml). The washed organic layer is dried and concentrated. The residue is then separated and purified by silica gel column chromatography to obtain white product of Biolimus A9 (0.48 g, 0.49 mmol), with a yield of 44.5%.

EXAMPLE 4

Comparative Example for Simulative Process Amplification of Example 3B

In a reaction flask, sirolimus (10 g, 10.9 mmol), ethyl di-isopropyl amine (78 g, 603.5 mmol), methylene chloride (35 ml) and 2-ethoxyethyl triflate (20 g, 88 mmol), each having a quantity about 10 times of that used in Example 3B, were added into the flask, which is filled with nitrogen gas. The reaction mixture is heated to 60° C. and is agitated for one hour and twenty minutes. Then, it is cooled, added with ethyl acetate (500 ml) and aqueous solution of hydrochloric acid (1N, 500 ml) and is further agitated. After agitation, it is settled for separating the layers. The organic layer is collected and respectively washed with pure water (500 ml), saturated saline (400 ml). The washed organic layer is dried and concentrated. The residue is then separated and purified by silica gel column chromatography to obtain white product of Biolimus A9 (2.9 g, 2.9 mmol), having a yield of 26.8% only.

Comparatively, via this process amplification, the yield of Biolimus A9 of the prior art is remarkably reduced in comparison with its small-scale production (Example 3B). Therefore, the prior art of U.S. Pat. No. 7,193,078 may be considered as a process especially suitable for small-scale production, such as a laboratory experiment, rather than a large-scale commercial or industrial production, which is thus inferior to this application, when compared with this application which has shown the high yields both in small-scale process (Example 1) and large-scale process (Example 2).

Accordingly, this application is more suitable for commercialization for mass production.

Moreover, the essential reactant of 2-ethoxyethyl triflate of the prior art (U.S. Pat. No. 7,193,078), even having high activity, is unstable because it will be decomposed into unknown compounds after one-week storage (by NMR spectrographic detection) as accompanied with physical change from its original colorless transparent liquid to a black viscous oily product, to thereby be inferior to this application because the 2-ethoxyethyl pentafluoro benzene sulfonate (which is obviously different from the 2-ethoxyethyl triflate as used in the prior art) of this application is still stable after one-week storage as aforementioned.

Furthermore, the 2-ethoxyethyl pentafluorobenzene sulfonate of this application may absorb ultra-violet rays to have a better tractability during the process proceeding than that of the 2-ethoxyethyl triflate (which is not UV-absorbable) of the prior art. So, this application is also beneficial for better production scheduling, reliable process tracking and efficient production management than the prior art.

So, this application is more suitable for commercial production even when considering the stability of product storage and improvement of process monitoring, control and management.

EXAMPLE 5

The Biolimus A9, as obtained from Example 2, is respectively added with anti-oxidant, namely Butylated Hydroxytoluene (or BHT), for 0.1%, 0.2, 0.5%, and 1% (w/w) based on 100% (wt) of Biolimus to enhance its stability at 40° C. by revealing a high yield of more than 99.4% even after six-week storage. Comparatively, a control test is provided by adding 0% of anti-oxidant (BHT) into Biolimus A9, resulting in a reduction of yield to be 69.7% after six-week storage. The yield data of different amounts of anti-oxidant as added into Biolimus A9 with respect to time lapse of weeks are summarized in Table 1 as below-mentioned.

TABLE 1

Stability of Biolimus A9 at 40° C.

| BHT (w/w) | Purity (%) of Biolimus A9 | | | |
|---|---|---|---|---|
| | 0 week | 2 weeks | 4 weeks | 6 weeks |
| 0.0% | 99.7 | 98.2 | 88.4 | 69.7 |
| 0.1% | 99.7 | 99.5 | 99.5 | 99.5 |
| 0.2% | 99.6 | 99.6 | 99.5 | 99.5 |
| 0.5% | 99.6 | 99.5 | 99.4 | 99.4 |
| 1.0% | 99.6 | 99.5 | 99.4 | 99.4 |

※ based on 100% (wt) of Biolimus A9

Accordingly, the Biolimus A9 as obtained by the present invention may be further added with anti-oxidant (preferably selected from BHT) to enhance its stability for long-time storage. The present invention may be further modified without departing from the spirit and scope of the present invention.

We claim:

1. A process for making Biolimus A9 represented by formula (1),

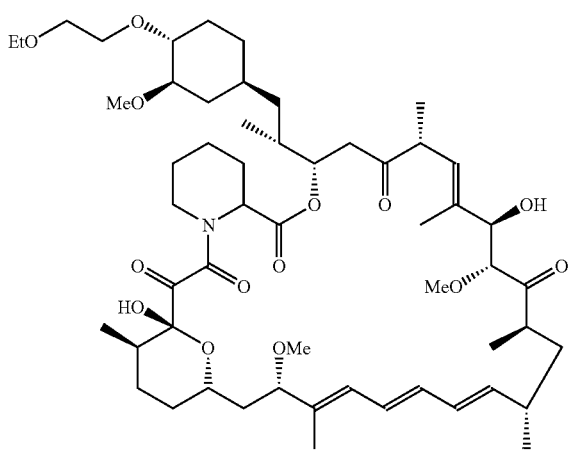

comprising reacting sirolimus of formula (2),

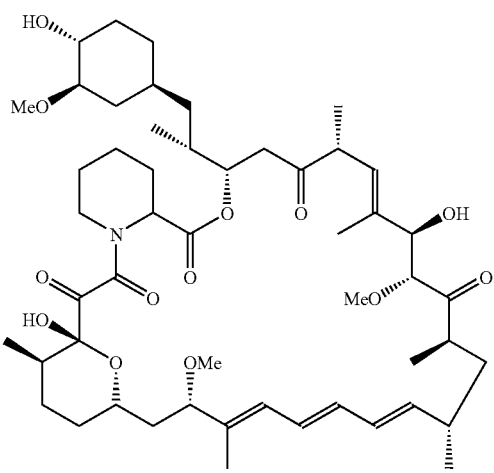

with
2-ethoxyethyl pentafluorobenzene sulfonate
under catalyzing by an organic base,
and in the presence of an organic solvent,
to undergo a nucleophilic substitution reaction to obtain Biolimus A9 of formula (1).

2. A process according to claim 1, wherein said 2-ethoxyethyl pentafluorobenzene sulfonate as used in the reaction is 1~20 moles per mole of said sirolimus of formula (2).

3. A process according to claim 1, wherein said organic base is trialkyl amine of formula (4),

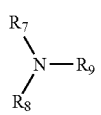

wherein: $R_7$, $R_8$ and $R_9$ are respectively selected from $C_1$~$C_{10}$ alkyl groups.

4. A process according to claim 3, wherein said triakyl amine is ethyl di-isopropyl amine.

5. A process according to claim 1, wherein said organic base is pyridine of formula (5)

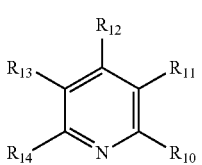

wherein: $R_{10}$~$R_{14}$ are respectively selected from: hydrogen, and $C_1$~$C_{10}$ alkyl groups.

6. A process according to claim 5, wherein said pyridine is 2, 6-dimethyl pyridine.

7. A process according to claim 1, wherein said organic base as used in the reaction is 20~80 moles per mole of said sirolimus.

8. A process for making Biolimus A9 as set forth in claim 1, wherein said Biolimus A9 thus obtained is further added with an anti-oxidant therein for enhancing a storage stability of said Biolimus A9.

9. A process according to claim 8, wherein said anti-oxidant is selected from: Butylatd hydroxytoluene (BHT), DL-α-tocopherol, propyl gallate, ascorbyl palmitate, 3-tert-butyl-4-hydroxy anisole, 2-tert-butyl-4-hydroxyanisole, and fumaric acid.

10. A process according to claim 8, wherein said anti-oxidant is butylated hydroxytoluene (or BHT).

11. A process according to claim 8, wherein said anti-oxidant as used is 0.01%~1.0% (by weight) based on 100% (by weight) of said Biolimus A9.

* * * * *